US010591426B2

(12) United States Patent
Miljak et al.

(10) Patent No.: US 10,591,426 B2
(45) Date of Patent: Mar. 17, 2020

(54) APPARATUS FOR ON-LINE DETECTION OF MAGNETIC RESONANCE SIGNALS FROM A TARGET MATERIAL IN A MINERAL SLURRY

(71) Applicant: COMMONWEALTH SCIENTIFIC AND INDUSTRIAL RESEARCH ORGANISATION, Acton, Australian Capital Territory (AU)

(72) Inventors: David Geoffrey Miljak, Jannali (AU); Peter John Coghill, Mortdale (AU); Jochen Lehmann-Horn, Meudon (FR); Bojan Lovric, Broadview (AU); Richard Yong, Mascot (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 98 days.

(21) Appl. No.: 15/754,489

(22) PCT Filed: Aug. 24, 2016

(86) PCT No.: PCT/AU2016/050776
§ 371 (c)(1),
(2) Date: Feb. 22, 2018

(87) PCT Pub. No.: WO2017/031537
PCT Pub. Date: Mar. 2, 2017

(65) Prior Publication Data
US 2018/0246047 A1    Aug. 30, 2018

(30) Foreign Application Priority Data

Aug. 24, 2015 (AU) .................................. 2015903417

(51) Int. Cl.
*G01N 24/08* (2006.01)
*G01V 3/14* (2006.01)
(Continued)

(52) U.S. Cl.
CPC ......... *G01N 24/085* (2013.01); *G01N 24/081* (2013.01); *G01R 33/3628* (2013.01); *G01R 33/422* (2013.01); *G01V 3/14* (2013.01)

(58) Field of Classification Search
CPC .. G01N 24/085; G01N 24/081; G01R 33/422; G01R 33/3628; G01V 3/14
See application file for complete search history.

(56) References Cited

U.S. PATENT DOCUMENTS

2005/0104593 A1   5/2005 Laubacher
2008/0036462 A1   2/2008 Schiano
(Continued)

FOREIGN PATENT DOCUMENTS

WO    WO2011/066600    6/2011

OTHER PUBLICATIONS

Written Opinion and International Search Report issued in connection with International Application No. PCT/AU2016/050778, dated Oct. 27, 2016. (Year: 2016).*

(Continued)

*Primary Examiner* — Susan S Lee
(74) *Attorney, Agent, or Firm* — Cooper & Durham LLP

(57) ABSTRACT

Apparatus including an electrically conductive housing, an electrically non-conducting pipe carrying the slurry through the housing, one or more primary coils each encircling the pipe within the housing and having a capacitor unit coupled thereto with a capacitor unit value chosen so that a primary coil series resonance is formed close to the value of a target magnetic resonance frequency, and for each primary coil, a drive coil and associated electrical network positioned to (Continued)

magnetically couple the drive coil to that primary coil. An impedance monitor coupled to each electrical network measures a complex input impedance thereof. An RF transmitter transmits a signal to one or more of the electrical networks with a frequency approximately equal to the target magnetic resonance frequency, and an RF receiver receives from each electrical network magnetic resonance signals from the target and forms an output signal of detected signals.

20 Claims, 3 Drawing Sheets

(51) Int. Cl.
*G01R 33/36* (2006.01)
*G01R 33/422* (2006.01)

(56) References Cited

U.S. PATENT DOCUMENTS

2012/0242340 A1 9/2012 Miljak
2013/0308753 A1* 11/2013 Groves ............... E21B 49/06
378/54

OTHER PUBLICATIONS

J. A Lehmann-Horn et.al: "Rapid detection of arsenic minerals using portable broadband NQR". The 3rd EAA European Congress on Acoustics, vol. 41, No. 19, Aug. 28, 2014.

Joel Mispelter et.al: "Coupling the Alderman-Grant resonator to the spectrometer, a practical design" in NMR Probeheads for Biophysical and Biomedical Experiments, Jan. 1, 2006 Imperial College Press.
Hoult D et.al: "Use of mutually inductive coupling in probe design" Concepts in Magnetic Resonance, vol. 15, Jan. 2, 2002.
Bennett, et al."On-Line Measurement of Mineralogy for OreSorting and Characterisation", In Applied Mineralogy:Developments in Science and Technology, ed Pecchio et al. (2004).
Kruukka, et al. "Kiruna mineral processing starts underground—Bulk sorting by LIF." CIM Bulletin 95(1066): 79-84 (2002).
Bennett, et al. "Quantitative Measurement of Copper Mineralogy Using Magnetic Resonance", Mineral Engineering, V20, pp. 1344-1350 (2007).
Bennett, et al. "The measurement of chalcopyrite in rocks and slurries using magnetic resonance", Mineral Engineering, V22, pp. 821-825 (2009).
Shultz, et al. "Quantitative aspects of nuclear quadrupole Resonance spectrometry of inorganics and minerals",Analytical Chemistry, V41 (4) p. 661 (1969).
Shultz, et al., "Applications of Nuclear Quadrupole Resonance Spectrometry to Analytical Chemistry", Applied Spectroscopy, V25 (3) p. 293 (1971).
Karr JR, et al. "Wide-line nuclear magnetic resonance spectroscopy of sulphur-33 in minerals", Spectroscopy Letters, V1 (5) p. 205 (1968).
Abdullin, et al. "Investigation of copperminerals by NQR: clystal-lochemistly, electronic structure, lattice dynamics", Phys Chem Min., V14 p. 258 (1987).

* cited by examiner

APPARATUS FOR ON-LINE DETECTION OF MAGNETIC RESONANCE SIGNALS FROM A TARGET MATERIAL IN A MINERAL SLURRY

CROSS REFERENCE TO RELATED APPLICATIONS

This application is a § 371 national stage of PCT International Application No. PCT/AU2016/050776, filed Aug. 24, 2016, claiming priority of Australian Patent Application 2015903417, filed Aug. 24, 2015, the contents of each of which are incorporated herein by reference in their entireties.

TECHNICAL FIELD

Embodiments generally relate to an apparatus and a method for on-line detection of magnetic resonance signals from a target material in a mineral slurry. The detected signals may then be processed to determine quantitative mineral slurry measurements, for instance the mass or concentration of the target material within a volume of the mineral slurry.

BACKGROUND

As used herein, mineral slurries are fluid mixtures of ground ore with water, where the ground ore particle size is generally less than 200 microns. A number of different ore minerals may be represented in a slurry. Froth flotation is a highly versatile method for physically separating particles based on differences in the ability of air bubbles to selectively adhere to specific mineral surfaces in a mineral/water slurry. The particles with attached air bubbles are then carried to the surface and removed, while the particles that remain completely wetted stay in the liquid phase. Froth flotation can be adapted to a broad range of mineral separations, as it is possible to use chemical treatments to selectively alter mineral surfaces so that they have the necessary properties for the separation. A large proportion of the world's base metal production is processed through flotation cells.

The optimisation of the flotation process is often dependant on the mix of ore mineralogies presented to the process, and not just the grade of the economic metal. There are a number of techniques that may be used to measure the composition of mineral slurries to aid process control. For example, representative sampling of slurries may be performed, where the samples are relayed to a laboratory for analysis of elemental and mineral composition using standard off-line techniques. However this approach often involves unavoidable delays that render the sampled data un-usable for short term process control.

To compensate for the delay, on-line slurry analysers have been developed. Within the context of the present invention, the expression "on-line" is used to indicate that magnetic resonance signals are obtained from certain materials in the mineral slurry as it passes through a pipe or the like. As a result, signal processing is able to occur on site, in real-time. In contrast, off-line analyses require that a sample of the slurry material be taken away for analysis.

The use of magnetic resonance sensors for quantitative detection or characterisation of minerals has been demonstrated in the laboratory. More recently the development of apparatus employing principles of magnetic resonance for on-line quantitative mineral slurry measurements has been attempted. One problem associated with mineral slurry measurements is that a varying amount of mineral particles pass at a variable flow rate through any such sensing apparatus. As a result, the varying solid material loading and composition affects the stability of the electrical load of a magnetic resonance sensor. In the same way, variability in the electrical conductivity of the slurry fluid phase can affect the stability of the electrical load. In the absence of electrical load control, the electrical load variation leads to an imperfect tuning-matching condition and reduces the radio frequency power transfer to and from the sensor. Variation of the electrical load may also lead to variations in the transfer function between sensor and receiver. The result is a loss of sensitivity and incorrect prediction of mineral concentration.

Other examples of on-line slurry analysers include X-ray fluorescence (XRF) analysers for the measurement of elemental concentration and on-line X-ray diffraction (XRD) analysers for the measurement of mineral phases. However such analysers may have some limitation for use in process control. For example, XRF analysis may not be able to be used to infer mineral phase concentration, while XRD analysis may suffer from inadequate detection limits in some circumstances. It would therefore be of benefit to the mineral processing industry if improved sensors and/or apparatus compatible with on-line slurry measurement could be developed.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

An apparatus for on-line detection of magnetic resonance signals from target materials in a mineral slurry is provided, the apparatus comprising:
  an electrically conductive housing;
  an electrically non-conducting (ENC) pipe to enable throughput of a mineral slurry, the ENC pipe configured to pass through the electrically conductive housing;
  at least a first primary coil configured to encircle a section of the ENC pipe within the housing, the or each primary coil defining a measurement zone;
  a capacitor unit coupled to a terminal of the or each respective primary coil, where a value of the or each capacitor unit value is selectable so that a primary coil series resonance is formed close to the value of the magnetic resonance frequency of the target material;
  an RF transmitter operable to transmit a signal to one or more drive coil electrical networks, where an operating frequency of the RF transmitter is set approximately equal to the magnetic resonance frequency of the target material;
  at least a first drive coil and an associated drive coil electrical network, where the number of drive coils equals the number of primary coils, and where each drive coil and associated drive coil electrical network is positioned relative to a single primary coil to magnetically couple said drive coil to said primary coil;

an impedance monitor coupled to each drive coil electrical network and operable to measure a complex input impedance of said drive coil electrical network; and an RF receiver adapted to receive from the first or each drive coil electrical network, magnetic resonance signals from the target material, the RF receiver forming an output signal of detected signals.

As configured, the apparatus is operable to separately set the phase angle of the drive coil electrical network impedance to a predetermined value. In another embodiment (described below), the apparatus is operable to separately set both the phase angle and magnitude of the drive coil electrical network impedance to a predetermined value. In either embodiment, the operability, coupled with the specific aspects of the apparatus described above, enabled the inventors to determine that this solves the problem of stabilising the transfer function between induced magnetic resonance sensor voltages and RF receiver voltages. Embodiments of the invention are thus highly advantageous as in the context of an online environment, as one would expect to see changes in the material loading in the pipe which may result in variability of the electrical transfer function.

The drive coil electrical network (complex) input impedance $Z_{in}$ may be written as $$Z_{in} = |Z_{in}| e^{i\varphi} \quad (1)$$

where $|Z_{in}|$ is the impedance magnitude and $\varphi$ the impedance phase angle. It is advantageous that $Z_{in}$ be held constant under varying application conditions. Therefore a predetermined $|Z_{in}|$ and $\varphi$ are sought to define the constant value of $Z_{in}$. In particular it is further advantageous that the predetermined $\varphi$ is approximately zero ($Z_{in}$ essentially purely real) and $|Z_{in}|$ equals a preferred standard system resistance $R_o$ (for example 50 ohms). For the apparatus described, there is a connection between $Z_{in}$ and the primary coil impedance because of the mutual coupling between the drive coil(s) and primary coil(s). Changes in either the real or imaginary parts of the primary coil impedance generally induce changes in both $|Z_{in}|$ and $\varphi$.

In some embodiments, the, or each, capacitor unit may be adjustable to modify the capacitor unit value. In the configuration of the apparatus described this has the effect of being able to modify substantially just the phase angle of the drive coil network impedance. In some embodiments the capacitance of each capacitor unit may be adjusted by mechanical means using, for example, a motor driven variable capacitor. The capacitance may also be adjusted through modification of coupled circuit terminations by electronic means. The capacitor modification required to match the input impedance phase angle to a predetermined value may be determined by comparing the measured input impedance phase angle to the predetermined value, and computing the required capacitance change $\Delta C$ based on a known relationship between the capacitance and the measured phase angle.

In one example of a drive coil network, a series resonant circuit may be formed with the drive coil, where the series resonance so formed is close to the primary coil series resonance. In this exemplar class of drive coil network, the relationship between required capacitance change $\Delta C$ and measured phase angle $\varphi$ may be approximated as $$\Delta C = -\sin(\varphi - \varphi_o)\left(\frac{1}{\omega^2 L Q}\right), \quad (2)$$

where $\varphi_o$ is the predetermined phase angle of approximately zero radians, $\omega$ is the operating angular frequency, L the primary coil inductance and Q the targeted fixed primary coil quality factor, where $Q = \omega L / r$, and where r is the primary coil resistance. Equation (2) has validity where variation of the parameter $\gamma = (|Z_{in}| - R_o)/R_o$ is moderate, which is true for many applications. Nonetheless Equation (2) can still be usefully employed at larger values of $\gamma$, or modified equations taking account of large $\gamma$ can be used.

Actuators may be used to vary the capacitance by the required value of $\Delta C$, where a known relationship between actuator position and capacitance, such as an approximately linear relationship, is known.

In some embodiments, the apparatus may further comprise a load coil with a fixed termination, the load coil positioned relative to the primary coil to magnetically couple the load coil to the primary coil. Changes in orientation of the load coil will result in changes in the impedance of the primary coil. Persons skilled in the art will appreciate that certain load coil terminations will result in variation of essentially only the real part of the primary coil network input impedance. For example, load coil terminations that act to series resonate the load coil at frequencies near the primary coil resonance frequency, together with additional termination series resistance, will act to contribute mainly a resistive change $\Delta r$ to the primary coil. Because of the magnetic coupling between drive coil and primary coil, and primary coil and load coil, the magnitude of the drive coil network input impedance may be modified to match a predetermined value by changing the orientation of the load coil. Assuming the class of drive coils used as an example previously, the required value of $\Delta r$ to obtain the predetermined magnitude $R_o$ is approximately given by $$\Delta r = -(|Z_{in}| - R_o)\left(\frac{\omega^2 M^2}{|Z_{in}| R_o}\right), \quad (3)$$

where M is the fixed mutual coupling between drive and primary coils. Equation (3) has validity at small to moderate values of $\varphi$.

The required orientation of the load coil (to achieve the value of $\Delta r$ in turn required to obtain the predetermined magnitude) may thus be determined by comparing the measured magnitude of the input impedance to the predetermined value using for example, equation 3, and computing the required orientation based on a known relationship between the orientation and the size of $\Delta r$. Therefore the orientation of the load coil is effectively determined by the measurement of the drive coil network impedance magnitude and its comparison to the predetermined value.

Actuators may be used to change the orientation of the load coil to obtain the required value of $\Delta r$, where a known relationship between actuator position and $\Delta r$, such as an approximately linear relationship, is known.

Equations (2) and (3) demonstrate that variation of $\Delta C$ can be used to modify essentially just the phase angle of the drive coil network input impedance, while variation of $\Delta r$ can be used to modify essentially just the magnitude of the drive coil network input impedance. In this sense the drive coil load phase angle and magnitude variations are decoupled from each other.

The RF excitation transmitted to one or more drive coil electrical networks may comprise either a Hahn pulse sequence or a wideband amplitude and phase modulated pulse sequence.

The RF transmitter and the RF receiver may be distinct units or may be integrated as an RF transceiver. The RF transmitter and the RF receiver may be incorporated into an RF transceiver unit which further includes a system controller to control switching between the transceiver mode and the receiver mode.

The RF transmitter may be operable to repetitively apply a radio frequency pulse sequence to a terminal of the or each of the drive coil electrical networks, where the transmitter operating frequency is set approximately equal to a target magnetic resonance frequency. It will be appreciated that the RF transmitter operating frequency is set approximately equal to a target magnetic resonance frequency, so as to induce a change in the nuclear spin magnetisation in the target material in the slurry. A variety of RF pulse sequences may be used to induce a radiofrequency nuclear magnetisation. For example, the Hahn echo sequence may be employed. Subsequent radio frequency signal voltages are generated at the drive coil network terminals due to the dynamic evolution of magnetisation in the target material.

In some embodiments, the apparatus further comprises at least one auxiliary coil magnetically coupled predominantly to a single primary coil, where the voltage at the terminal of the auxiliary coil is measured during the application of pulse sequences to the or each drive coil networks. The magnitude of the detected voltage is proportional to the primary coil current. In turn, the primary coil current strongly affects the induced MR signal. The auxiliary coil voltage may be used to apply feedback to the transmitter to stabilise the primary coil current. Such an embodiment is advantageous as variable transmitter power may cause variation in the generated magnetic resonance signal voltage.

In some embodiments, the apparatus further comprises at least one auxiliary coil magnetically coupled predominantly to a single primary coil, where the voltage at the terminal of the auxiliary coil is measured during the application of pulse sequences to the or each drive coil networks and the magnitude of the detected voltage is compared against a reference voltage magnitude, where the difference between the measured and reference voltage magnitudes is used to control the output power of the RF transmitter such that the magnitude of the detected voltage equals a predetermined value.

The at least one primary coil may be a single turn split loop, a solenoid or an Alderman Grant resonator. Persons skilled in the art will appreciate that other coil configurations that encircle the pipe are possible and therefore the invention is not limited to the examples specified.

The capacitor unit may be composed of multiple individual capacitors arranged in series or parallel arrangement. One or more of the individual capacitors may be a trimmer capacitor.

The primary coil and its capacitor are situated entirely inside the housing. It will be appreciated that none of the primary coils or capacitor units make any conductive connection to the housing or any other conductor. This configuration aids in minimising effects due to sensor common mode voltages that may introduce conservative electric fields over the slurry volume.

In some embodiments where the apparatus comprises two or more primary coils, the second and/or subsequent primary coils are configured to encircle different sections of the ENC pipe within the housing. In such an embodiment, each primary coil is associated with a separate capacitor unit. In such an embodiment, each primary coil may be series tuned at a magnetic resonance frequency of the selected target materials. Each primary coil may be tuned to a separate target material. In some embodiments, multiple coils may be tuned to the same target material in order to increase sensitivity for the said target material.

In some embodiments, the regions around each primary coil may be separated by electrically conducting septums, each of said electrically conducting septums configured to be integrated into the housing.

The apparatus may further comprise storage means to store the output signal of the detected signals. Persons skilled in the art will appreciate that there are many different methods of configuring the transceiver for the purpose of signal detection and subsequent electronic storage.

The apparatus may further comprise a processing unit to process the output signal of detected signals to determine the mass or concentration of the target material in the mineral slurry passing through the measurement zone(s).

In some embodiments the apparatus may be further configured to apply a static magnetic field of less than 100 mT to the slurry material in the region enclosed by the primary coil. In some embodiments the apparatus may further comprise one or more magnets, each magnet configured to apply a static magnetic field to the slurry material in the region enclosed by the or each primary coil. Each static magnetic field may be generated by an electromagnet or by a permanent magnet. The application of a static magnetic field advantageously lengthens the spin-spin decay time of the magnetic resonance.

A method is provided for on-line detection of magnetic resonance signals from a target material in a mineral slurry using an apparatus as described in any one of the embodiments above, the method comprising:

separately setting the respective phase angles and magnitudes of the or each drive coil electrical network impedance to a predetermined value.

The method may further comprise first setting the phase angle of the or each drive coil network input impedance to a predetermined value and then setting the magnitude of the drive coil network input impedance to a predetermined value.

The method may further comprise magnetically coupling a load coil to a distinct primary coil, and changing the orientation of the load coil to modify the magnitude of the drive coil network input impedance to match a predetermined value.

The method may further comprise comparing the measured magnitude of the input impedance to the predetermined value, and computing the required orientation based on a known relationship between the orientation and the magnitude of the input impedance.

The method may further comprise measuring the temperature of the slurry and compensating the received magnetic resonance signal using a known dependence of signal magnitude with temperature.

The method may further comprise magnetically coupling at least one auxiliary coil predominantly to a single primary loop, and measuring the voltage at the terminal of the auxiliary loop during the application of radio frequency pulse sequences to the drive coil network. In some embodiments the method may further comprise using the auxiliary loop voltage to apply feedback to the transmitter to stabilise the primary coil current. In some embodiments, the method may further comprise measuring the magnitude of the detected voltage against a reference magnitude, determining a difference between the measured and reference magnitudes and using the difference in magnitudes to control the output power of the RF transmitter such that the magnitude of the detected voltage equals a predetermined value.

The method may further comprise measuring the mineral slurry's temperature and adjusting the transmitter's operating frequency to substantially align with the predicted magnetic resonance frequency.

This embodiment is advantageous as the magnetic resonance frequency may vary according to the temperature of the target material. In addition, the measured temperature may also be used to compensate signals due to the known Boltzmann factor associated with magnetic resonance detection.

The method may further comprise storing the output signal of detected signals.

The method may further comprise processing the output signal of detected signals to determine the mass or concentration of the target material in the mineral slurry passing through the measurement zone(s).

Persons skilled the art will appreciate that there are a variety of signal metrics and processing techniques that may be used to determine the mass of target material. For example, the peak magnitude of a generated spin echo may be estimated from the output signal and assumed to be proportional to the mass of target material. In addition, the output signal may also be normalised according to the total mass of all solids in the primary coil measurement zone to determine the solids weight percentage or concentration of a target material. The total mass of all solids in the slurry may be obtained by measuring the solids materials in the slurry using, for example, a slurry density analyser. An example of a procedure to determine the concentration is as follows:

$$C_m = \alpha \frac{\langle S \rangle}{\langle M \rangle},$$

where $C_m$ is the average concentration of the target material over a chosen integration time, $\alpha$ is a fixed calibration factor, S, M are the instantaneous signal and mass solids loading respectively, and where the brackets denote the time average value over the integration time. Persons skilled in the art will appreciate that there are a variety of methods available to transmit consecutive computed $C_m$ values to other plant equipment for use in on-line applications.

BRIEF DESCRIPTION OF DRAWINGS

Embodiments are described in further detail below, by way of example, and with reference to the accompanying drawings, in which.

DETAILED DESCRIPTION

Herein the term "magnetic resonance" (MR) refers to both Nuclear Magnetic Resonance (NMR) and Nuclear Quadrupole Resonance (NQR). NMR and NQR are methods having wide application in measurement and characterisation of solid and liquid materials. These methods are routinely used as a laboratory tool to investigate bonding and molecular structure. They have also found use in real-time detection and characterisation of minerals and other substances such as narcotics or explosives. There are many classes of NMR and NQR; for example, zero-field NMR, NMR of magnetically ordered materials (i.e ferromagnetic NMR, anti-ferromagnetic NMR) or double resonance NQR. For the purposes of the specification, all subclasses of NMR or NQR are included in the term "magnetic resonance" (MR).

Embodiments generally relate to an apparatus for on-line detection of magnetic resonance signals from a target material in a mineral slurry. The target material may have a magnetic resonance frequency ranging between 1-200 MHz, relevant to most ore minerals.

Figure 1:
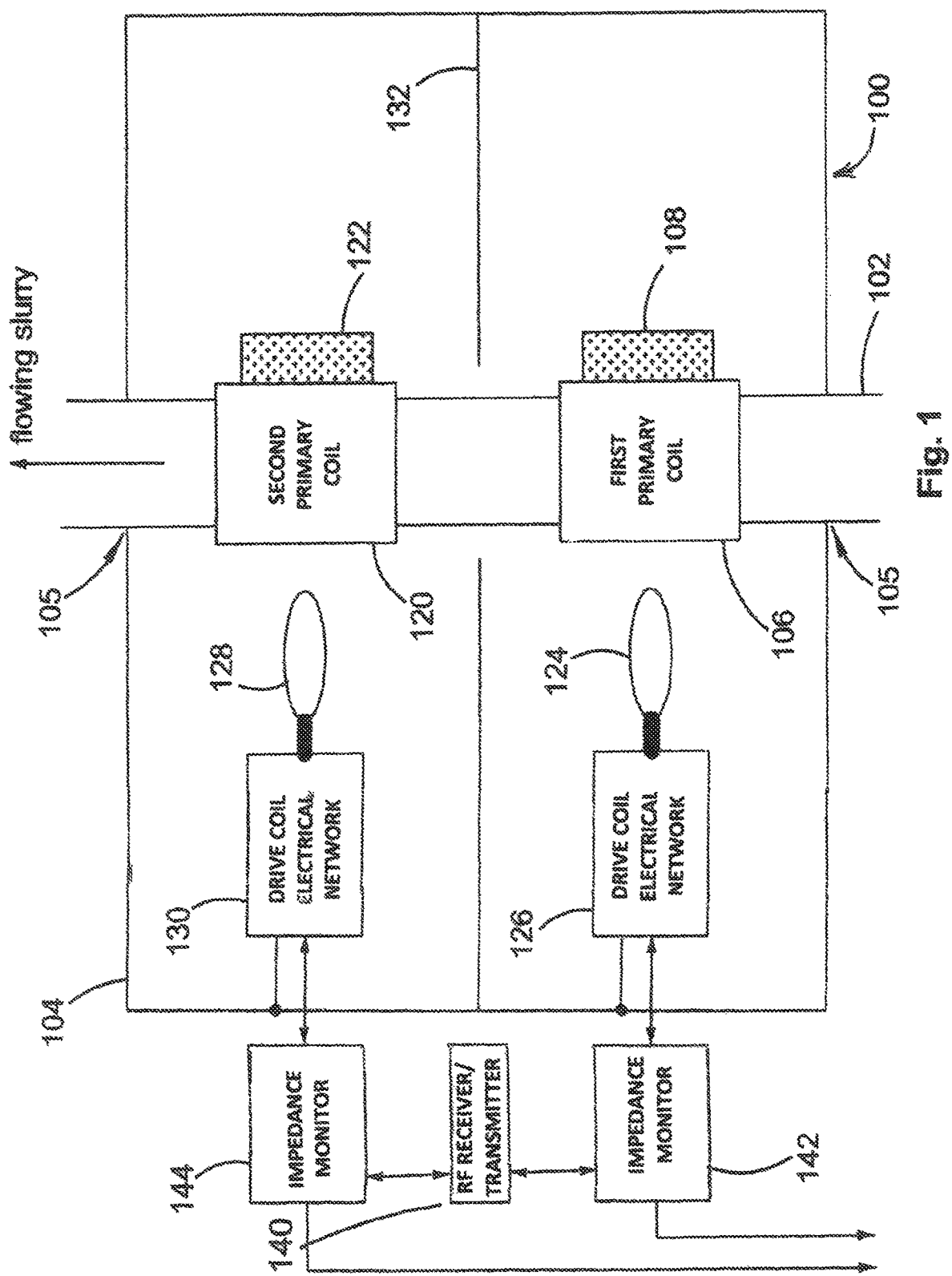
FIG. 1 is a schematic plan view of a first embodiment of a magnetic resonance apparatus in accordance with the invention.

FIG. 1 illustrates a first embodiment of a magnetic resonance (MR) apparatus 100 in accordance with the invention. The MR apparatus 100 includes an electrically non-conducting (ENC) pipe or conduit 102 which has a diameter of ~110 mm. The ENC pipe 102 carries a mineral slurry which is to be tested for the presence and concentration of a target material. An electrically conductive housing or enclosure 104 is positioned substantially around a section of the ENC pipe 102, and the ENC pipe 102 enters and exits the enclosure 104 through openings 105 therein. A first primary coil 106 encircles a section of the ENC pipe 102. A single capacitor unit 108 is placed across the terminal of the first primary coil 106. A second primary coil 120, spaced apart from the first primary coil 106 encircles a distinct section of the non-conducting pipe 102. Associated with the second primary coil 120 is a further capacitor unit 122 which is placed across the terminal of the second primary coil 120.

Each of the first primary coil 106 and its associated capacitor unit 108 and the second primary coil 120 and its associated capacitor unit 122 are completely inside the enclosure 104, and neither the first primary coil 106, the second primary coil 120 or their respective capacitor units 108 and 122 make any conductive connection to the enclosure 104 or any other conductor present in the apparatus 100.

The value of each of the capacitor units 108 and 122 is chosen so that a first primary coil series resonance and a second primary coil series resonance respectively is formed close to the value of a target magnetic resonance frequency, such that the frequency separation of the primary coil series resonance and the target magnetic resonance frequency is less than approximately 50% of the spectral width of the target magnetic resonance. The MR apparatus 100 further includes a first drive coil 124 and an associated drive coil electrical network 126 and a second drive coil 128 and an associated drive coil electrical network 130. Each of the drive coil and respective networks are positioned relative to the respective primary coils to magnetically couple each of the drive coils to their associated primary coil.

For each drive coil 124, 128 and associated drive coil electrical network 126, 130 the apparatus includes an impedance monitor 142, 144 each of which are operable to measure a complex input impedance of the respective drive coil network. Persons skilled in the art will appreciate that the input impedance to the drive coil network may be measured using a monitor comprised of various types of circuits. The drive coil network is excited by an RF transmitter in order to generate drive coil currents.

An electrically conducting septum 132 is integrated into the enclosure interposed between the first and second primary coils 106, 120. Use of a conducting septum 132 is advantageous in order to reduce or avoid capacitive coupling between the first and second primary coils 106, 120. It is typically convenient for the septum to be connected to the electrically conducting enclosure.

The MR apparatus 100 further includes an RF transmitter/receiver 140. The RF transmitter/receiver 140 is operable in a transmitter mode to transmit an RF signal in the form of a pulse sequence to one or more drive coil electrical networks, where an operating frequency of the RF transmitter is set approximately equal to the magnetic resonance frequency of the target material. The radio transmitter/receiver 140 is further operable in a receiver mode to receive from each of the drive coil electrical networks, magnetic resonance signals from the target material, the RF receiver forming an output signal of detected signals. The RF transmitter/receiver 140 includes a switch (not shown) to effect switching between a transmit and receive mode.

The output signal is subsequently processed to determine the mass or concentration of the target materials in the mineral slurry passing through the non-conducting pipe 102.

Figure 2:
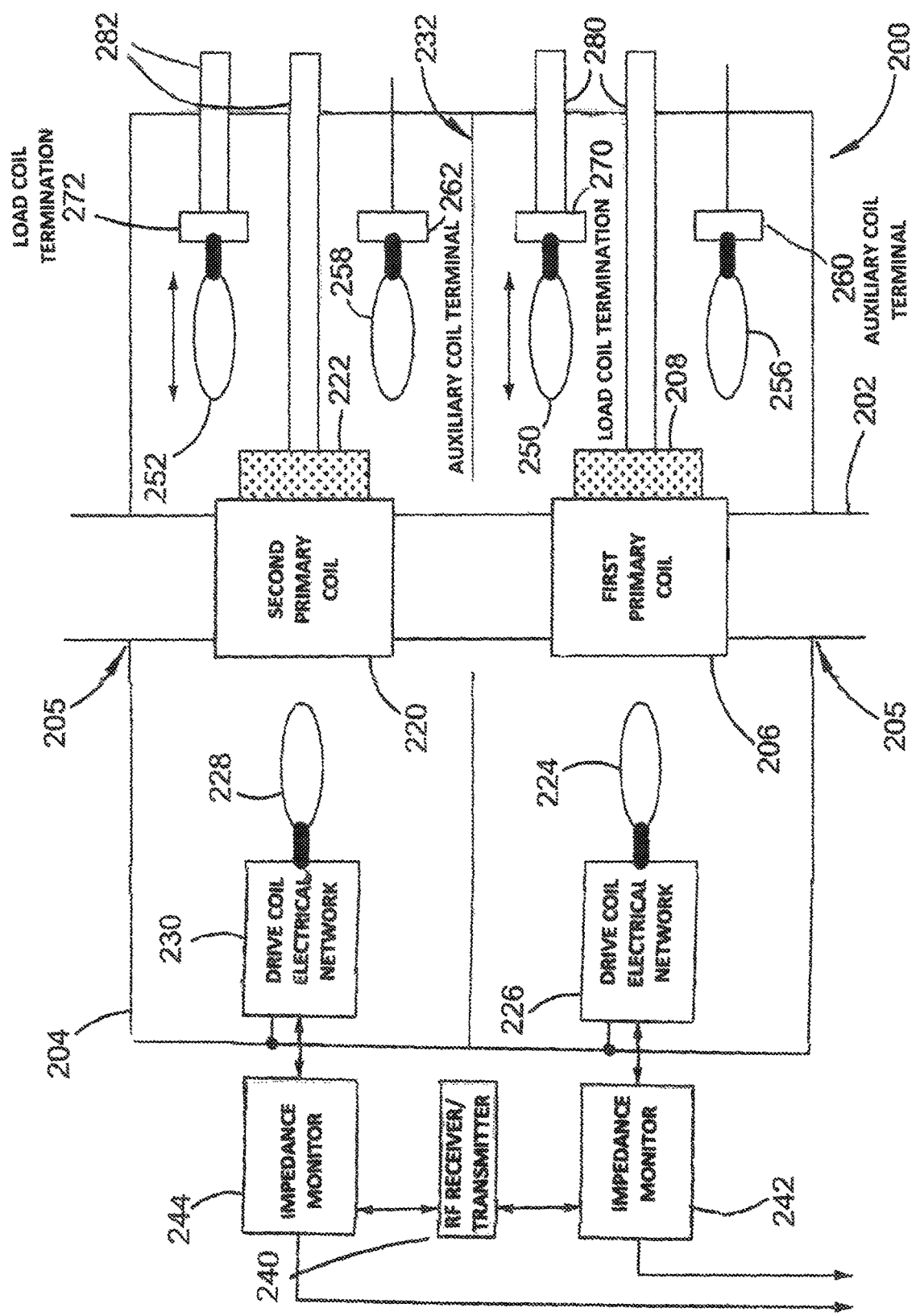
FIG. 2 is a schematic plan view of a second embodiment of a magnetic resonance apparatus in accordance with the invention.

FIG. 2 illustrates a second embodiment of a magnetic resonance (MR) apparatus 200 in accordance with the invention. As with the MR apparatus 100 illustrated in FIG. 1, the MR apparatus 200 includes a non-conducting pipe 202 which passes through openings 205 in a conductive enclosure 204. A first primary coil 206 encircles a section of the non-conducting pipe 202 and a capacitor unit 208 is placed across the terminal of the first primary coil 206. A second primary coil 220 spaced apart from the first primary coil 206, encircles a distinct section of the non-conducting pipe 202, and a further capacitor unit 222 is placed across the terminal of the second primary coil 220.

As with the MR apparatus 100 illustrated in FIG. 1, the first primary coil 206, its associated capacitor unit 208 and the second primary coil 220 and its associated capacitor unit 222 are completely inside the enclosure 104, and neither the first primary coil 206, the second primary coil 220 or their respective capacitor units 208 and 222 make any conductive connection to the enclosure 214 or any other conductor present in the apparatus 200.

The MR apparatus 200 further includes a first drive coil 224 and an associated drive coil electrical network 226 and a second drive coil 228 and an associated drive coil electrical network 230. For each drive coil 224, 228 and associated drive coil electrical network 226, 230 the apparatus includes an impedance monitor 242, 244 each of which are operable to measure a complex input impedance of the respective drive coil network. An electrically conducting septum 232 is integrated into the enclosure interposed between first and second primary coils 216, 220.

The MR apparatus 200 includes a radio transmitter/receiver 240 operable to (i) repetitively apply a radio frequency pulse sequence to each of the drive coil network terminals 226 and 230 and (ii) detect a radio frequency signal voltage generated at the drive coil network terminals due to the dynamic evolution of magnetisation in the target material.

In order to maintain effective quantitative measurement, it is desirous that the electrical transfer function between a series voltage in the primary coil, the drive coil and the RF receiver voltage be stabilised. Changes of material loading in the non-conducting pipe, or small changes in the selected operating frequency may result in transfer function variation. The inventors note that maintaining stability of the transfer function is a more stringent requirement than maintaining only a constant circuit input impedance at a single frequency, as occurs with most MR apparatus. The former requirement is essentially equivalent to maintaining both a constant drive coil impedance and a constant circuit Q.

A stable transfer function may be achieved to a good approximation by (i) keeping constant both the real and imaginary parts of the series impedance formed by the primary coil and the capacitor unit at the chosen operating frequency, and, (ii) at the same time, keeping the mutual impedance between primary coil and drive coil fixed. Under these circumstances the drive coil network input impedance will also exhibit stability. This stability may be obtained over a range of operating frequencies where the two conditions can be met, which in practice, can be made to exceed the operational frequency range required by the application. Persons skilled in the art will appreciate that judicious configuration of a drive coil network, such as the exemplar case previously discussed, and described by approximating equations (2)-(3), will allow for a one-to-one correspondence between the imaginary part of the primary coil series impedance and the phase angle of the drive coil network input impedance. Likewise, a one-to-one correspondence may be obtained between the real parts of the primary coil impedance and the magnitude of the drive coil network input impedance. The problem of transfer function stability is therefore reduced to the problem of separately setting the phase angle and magnitude of the drive coil network impedance to a predetermined optimal value. The decoupling of load phase angle and magnitude for obtaining load stability is a highly desirable attribute for control purposes.

The capacitance value of the capacitor unit 208 associated with the primary coil 206 is able to be mechanically varied to alter predominantly only the phase angle of the input impedance of the drive coil network 226 associated with the primary coil 206, so that the phase angle of the input impedance equals a predetermined value. Similarly, the capacitance value of the capacitor unit 222 associated with the second primary coil 220 is able to be mechanically varied. A known relationship between the capacitance value and the phase angle of the drive coil network input impedance is used to estimate the mechanical variation of the capacitance required to set the phase angle of the input impedance to a predetermined value. For example, for the case when the drive coil network forms a series resonant circuit with the drive coil, where the series resonance so formed is close to the primary coil series resonance, then the equation (2) approximation may be used to determine the required capacitance change.

Associated with each of the first and second primary coils 206 and 220, and magnetically coupled thereto is a respective load coil 250, 252. Load coil 250 has a load coil termination 270 and load coil 252 has a load coil termination 272. The magnitude of the drive coil network's 226 input impedance may be modified to match a predetermined value by changing the orientation of the load coil 250. Similarly, the magnitude of the drive coil network's 230 input impedance may be modified to match a predetermined value by changing the orientation of the load coil 252. Persons skilled in the art will appreciate that certain load coil terminations will result in variation of substantially only the magnitude of the drive coil network input impedance. The required orientation of the load coil 250 is determinable by comparing the measured magnitude of the input impedance to the predetermined value, and computing the required orientation based on a known relationship between the orientation and the magnitude of the input impedance.

For each primary coil 250, 252 there is provided an auxiliary coil 256, 258 which is magnetically coupled predominantly to a single primary loop. Each auxiliary coil 256, 258 has an auxiliary coil terminal 260, 262, where the voltage at the respective auxiliary coil terminal 260, 262 is measured during the application of radio frequency pulse sequences to the respective drive coil network 226, 230. In operation, the magnitude of the detected voltage is compared against a reference magnitude, and the difference between the measured and the reference magnitudes is used to control the output power of the radio frequency transmitter 240, so that the magnitude of the detected voltage equals a predetermined value.

The signal transfer function between each of the primary coils 206, 220 and the receiver 240 is stabilised through the intermittent use of actuators 280 and 282 that vary the value of the capacitance units 208 and 222 or the orientation of the load coil 250 and 252 associated with each primary coil 206 and 220. The actuators 280 and 282 are operated according to measurements of the input impedance of the respective drive coils 224 and 228, where actuator steps are calculated from known relationships. The phase angle of the drive coil network input impedance is set to a predetermined value, followed by the setting of the magnitude of the drive network impedance. This process is repeated at time intervals characteristic of the slurry process variation. At least one of the pairs of auxiliary coils 280 and 282 is also used to monitor the primary coil current in order to stabilise the output of the RF transmitter 240 over successive pulses.

Figure 3:
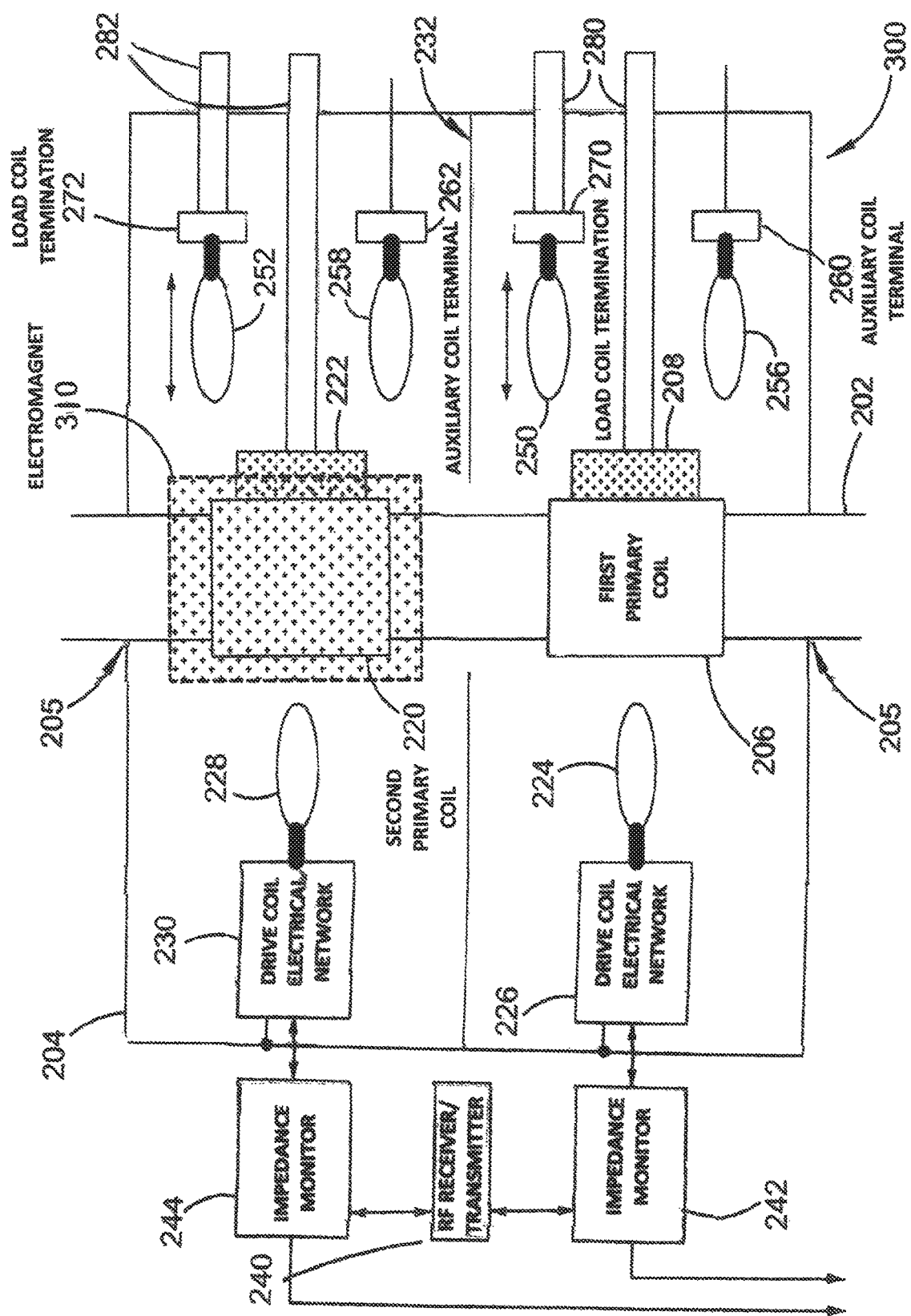
FIG. 3 is a schematic plan view of a third embodiment of a magnetic resonance apparatus in accordance with the invention.

FIG. 3 illustrates a third embodiment of a magnetic resonance (MR) apparatus 300 in accordance with the invention. Many of the elements correspond to those illustrated and described with respect to FIG. 2, accordingly like numerals indicate similar elements and will not be reiterated here.

For some target materials, a short spin-spin relaxation time $T_2$ causes a reduction in signal to noise ratio due to the fact that coil ringdown due to a finite Q interferes with attempted spin echo resolution in two-pulse excitation sequences. This problem may persist even after known methods used to reduce the ringdown have been implemented.

It is known that the spin-spin relaxation in quadrupolar spin resonances may be lengthened by application of a weak static field to the sample[1] that acts to weakly split the quadrupolar resonance and decouple otherwise coupled spins that contribute to $T_2$. The applied field is weak in the sense that the Zeeman term due to any externally applied static magnetic fields $H_{ext}$ in the Hamiltonian equation $H=H_q+H_{ext}+H_{int}$ is significantly smaller than the quadrupole term $H_q$ which is due to the interaction energy between the nuclear electric quadrupole moment and the local electric field gradient.

Accordingly, the apparatus 300 includes an electromagnet 310 configured to apply a static magnetic field of less than 100 mT to the slurry material in the region enclosed by the primary coil 220. Whilst only one electromagnet 310 is shown, it will be appreciated that a further electromagnet may be configured to apply a static magnetic field to the slurry material in the region enclosed by the primary coil 206.

In a specific embodiment of the apparatus (and with reference to FIG. 3), the non-conducting pipe 202 carries a mineral slurry at a solids loading of 30 wt %. The slurry contains the target minerals chalcopyrite and covellite.

Pulsed RF currents at an operating frequency of 18.5 MHz and 14.28 MHz, corresponding to the target frequency of the magnetic resonance at a temperature of 300K in the mineral chalcopyrite and covellite respectively, are applied to drive coil networks 226 and 230 coupled to two split loop primary coils 206 and 220 respectively. A Hahn pulse sequence is used to change the nuclear spin polarisation. Upon completion of the Hahn sequence, a spin echo is detected by way of induced voltage in the first and second primary coils 206 and 220. The signal voltages that couple to the drive coils 224 and 228 are detected by the radio receiver 240 and stored in memory (not shown). This measurement sequence for each target material is repeated indefinitely as slurry flows through the non-conductive pipe.

Processing of the signal involves averaging of sequences, and numerical methods used to extract estimates of peak echo magnitude for each target. The derived peak echo magnitudes are used to infer chalcopyrite and covellite mass within the primary coil sensing volume, by multiplying each targets' peak echo magnitude with a predetermined calibration factor. The concentration of chalcopyrite or covellite is then calculated by normalising the mineral mass with the slurry total mass loading, measured with a density gauge.

The signal transfer function between the primary coils 206, 220 and the receiver 240 is stabilised through the intermittent use of actuators 280, 282 that vary the value of the capacitance units 208, 222 or the orientation of the load coil 250, 252 associated with each primary coil 206, 220 respectively. The actuators 280, 282 are operated according to measurements of the input impedance of the respective drive coils, where actuator steps are calculated from known relationships For example, a drive coil impedance measurement may indicate a requirement for certain values of $\Delta C$ and $\Delta r$ to be applied to obtain predetermined impedance phase angle and magnitude. In turn, a known linear relationship between actuator positions and $\Delta C$ or $\Delta r$ may exist. The required actuator positions may then be computed from the known $\Delta C$ or $\Delta r$ by way of the known linear dependence of these parameters with actuator position. The actuator can be set to its calculated position to obtain the correct drive coil network input impedance. The phase angle of the drive coil network input impedance is set to a predetermined value, followed by the setting of the magnitude of the drive network impedance. This process is repeated at time intervals characteristic of the slurry process variation. An auxiliary coil is also used to monitor the primary coil current in order to stabilise the output of the RF transmitter over successive pulses.

The temperature of the slurry is measured (not shown) continuously and used to intermittently modify the operating frequency pertaining to each target, where the modification is determined from a known relationship between the target magnetic resonance frequency and temperature. The temperature may also be used to compensate signal magnitudes, based on known relationships between signal magnitude and temperature.

The apparatus 300 includes an electromagnet 310 configured to apply a static magnetic field of less than 100 mT to the slurry material in the region enclosed by the primary coil 220.

Electromagnet 310 applies a static magnetic field of up to 100 mT to the primary coil 220 sensing volume associated with covellite detection. This magnetic field acts to increase the spin-spin relaxation time of the covellite quadrupole magnetic resonance of the $^{63}$Cu nucleus at 14.28 MHz (at temperature 300 K). This increases the signal to noise ratio of the covellite measurement.

It will be appreciated by persons skilled in the art that numerous variations and/or modifications may be made to the above-described embodiments, without departing from the broad general scope of the present disclosure.

Whilst the embodiments illustrated in all figures shows a first primary coil and the second primary coil, it should be appreciated that optional embodiments may utilise subsequent coils, in which case the number of drive coils will equal the number of primary coils, where each drive coil network has a single terminal, where the drive coil is magnetically coupled to a single primary coil and where the complex input impedance of the drive coil network is measured.

The present embodiments are, therefore, to be considered in all respects as illustrative and not restrictive.

REFERENCES

1. E. L. Hahn and B, Herzog, "Anisotropic Relaxation of Quadrupole Spin Echoes", Physical Review, V 93, p 639 (1954)

The invention claimed is:

1. An apparatus for on-line detection of magnetic resonance signals from a target material in a mineral slurry, the apparatus comprising:
   an electrically conductive housing;
   an electrically non-conducting (ENC) pipe to enable throughput of a mineral slurry, the ENC pipe configured to pass through the electrically conductive housing;
   one or more primary coils configured to encircle a section of the ENC pipe within the housing, each primary coil defining a measurement zone;
   a capacitor unit coupled to a terminal of each respective primary coil, where a value of each capacitor unit value is selectable so that a primary coil series resonance is formed close to a value of a magnetic resonance frequency of the target material;
   an RF transmitter operable to transmit a signal to one or more drive coil electrical networks, where an operating frequency of the RF transmitter is set approximately equal to the magnetic resonance frequency of the target material;
   one or more drive coils each having an associated drive coil electrical network, where the number of drive coils equals the number of primary coils, and where each drive coil and associated drive coil electrical network is positioned relative to a single primary coil to magnetically couple said drive coil to said primary coil;
   an impedance monitor coupled to each drive coil electrical network and operable to measure a complex input impedance of said drive coil electrical network; and
   an RF receiver adapted to receive from each drive coil electrical network, magnetic resonance signals from the target material, the RF receiver forming an output signal of detected signals.

2. The apparatus according to claim 1, where each capacitor unit is configured to vary the respective capacitor's value in order to substantially alter only a phase angle of the input impedance of the drive coil network associated with the respective primary coil, such that the phase angle of the input impedance equals a predetermined value.

3. The apparatus as in claim 2, where a known relationship between a capacitance value and a phase angle of the drive coil network input impedance is used to estimate a variation required to set the phase angle of the input impedance to a predetermined value.

4. The apparatus according to claim 1, further comprising one or more load coils, where each load coil is magnetically coupled to a distinct primary coil, a terminating impedance of each load coil is fixed, and where an orientation of each load coil is operable to be adjusted to vary a magnetic coupling between the respective load coil and its primary coil.

5. The apparatus according to claim 4, where a change in orientation of the load coil substantially alters only a magnitude of the input impedance of said drive coil network, so that the magnitude of the input impedance equals a predetermined value.

6. The apparatus as in claim 5, where a known relationship between load coil orientation and the magnitude of the drive coil network input impedance is used to estimate the load coil orientation required to set the magnitude of the input impedance to a predetermined value.

7. The apparatus according to claim 1, where the impedance monitor is further operable to allow setting a phase angle of the drive coil network input impedance to a predetermined value and setting a magnitude of the drive coil network input impedance to a predetermined value.

8. The apparatus according to claim 1, where an excitation transmitted to one or more drive coil electrical networks comprises either a Hahn pulse sequence or a wideband amplitude and phase modulated pulse sequence.

9. The apparatus according to claim 8, further comprising at least one auxiliary coil magnetically coupled predominantly to a single primary coil, where a voltage at a terminal of the auxiliary coil is measured during the application of pulse sequences to each drive coil network.

10. The apparatus according to claim 1, where the RF transmitter and the RF receiver are incorporated into an RF transceiver unit which includes a system controller to control switching between a transmitter mode and a receiver mode.

11. The apparatus according to claim 1, where each primary coil is one of a single turn split loop, a solenoid and an Alderman-Grant resonator.

12. The apparatus according to claim 1, where the apparatus further comprises at least a second primary coil, and an electrically conducting septum integrated into the enclosure between a first primary coil and the second primary coil.

13. The apparatus according to claim 1, further comprising a temperature sensor arranged to measure a temperature of the slurry, where the apparatus is configurable to modify an operating frequency of the transmitter according to the measured temperature.

14. The apparatus according to claim 1, further comprising one or more magnets, each magnet configured to apply a static magnetic field to the slurry in the region enclosed by each primary coil.

15. The apparatus according to claim 14, where the static magnetic field is generated by an electromagnet or by a permanent magnet.

16. A method for on-line detection of magnetic resonance signals from a target material in a mineral slurry using an apparatus as claimed in claim 1, the method comprising:
   separately setting a respective phase angle and magnitude of each drive coil electrical network impedance to a predetermined value.

17. The method according to claim 16, further comprising setting the phase angle of each drive coil network input impedance to a predetermined value and setting a magnitude of the drive coil network input impedance to a predetermined value.

18. The method according to claim 16, further comprising magnetically coupling a load coil to a distinct primary coil, and changing an orientation of the load coil to modify a magnitude of a drive coil network input impedance to match a predetermined value.

19. The method according to claim 18, further comprising comparing a measured magnitude of an input impedance to the predetermined value, and computing a required orientation based on a known relationship between the orientation and the magnitude of the input impedance.

20. The method according to claim 16, further comprising magnetically coupling at least one auxiliary coil predominantly to a single primary loop, and measuring a voltage at a terminal of an auxiliary loop during the application of the RF signal to each drive coil network.

* * * * *